(12) United States Patent
Sahmkow et al.

(10) Patent No.: US 6,520,180 B1
(45) Date of Patent: Feb. 18, 2003

(54) DEVICE FOR MEASURING A BREATHING GAS COMPONENT IN A BREATHING GAS LINE

(75) Inventors: Dieter Sahmkow, Lübeck (DE); Tillmann von Blumenthal, Lübeck (DE); Bernhard Ludwig, Lübeck (DE); Dirk Fiebelkorn, Lübeck (DE); Hendrik Hantzko, Lübeck (DE)

(73) Assignee: Dräger Medizintechnik GmbH (DE)

( * ) Notice: Subject to any disclaimer, the term of this patent is extended or adjusted under 35 U.S.C. 154(b) by 30 days.

(21) Appl. No.: 09/714,720

(22) Filed: Nov. 16, 2000

(30) Foreign Application Priority Data

Mar. 25, 2000 (DE) .......................................... 100 14 959

(51) Int. Cl.$^7$ ............................................. A61M 16/00
(52) U.S. Cl. ............................ 128/204.21; 128/204.18; 128/205.11; 128/205.24; 128/204.22
(58) Field of Search ....................... 128/204.21, 204.22, 128/204.18, 205.11, 205.24

(56) References Cited

U.S. PATENT DOCUMENTS

| | | | | |
|---|---|---|---|---|
| 3,672,388 A | * | 6/1972 | Ringwall et al. | ....... 128/201.27 |
| 3,903,881 A | * | 9/1975 | Weigl | ................... 128/204.25 |
| 4,550,726 A | * | 11/1985 | McEwen | ............... 128/202.22 |
| 4,622,976 A | * | 11/1986 | Timpe et al. | ................. 600/431 |
| 4,939,647 A | * | 7/1990 | Clough et al. | .......... 128/201.27 |
| 5,048,515 A | * | 9/1991 | Sanso | ..................... 128/204.18 |
| 5,694,924 A | * | 12/1997 | Cewers | .................... 128/204.21 |
| 5,823,186 A | * | 10/1998 | Rossen et al. | .......... 128/203.12 |
| 5,848,591 A | * | 12/1998 | Weismann | .............. 128/204.22 |
| 5,850,835 A | * | 12/1998 | Takaki et al. | ........... 128/204.18 |
| 5,890,490 A | * | 4/1999 | Aylsworth et al. | ...... 128/203.12 |
| 6,095,137 A | * | 8/2000 | Wallroth et al. | ........ 128/203.26 |
| 6,152,131 A | * | 11/2000 | Heinonen | ............... 128/204.23 |
| 6,173,711 B1 | * | 1/2001 | Ruton | .................... 128/204.26 |
| 6,209,540 B1 | * | 4/2001 | Sugiura et al. | ......... 128/204.18 |
| 6,269,810 B1 | * | 8/2001 | Brooker et al. | ......... 128/203.12 |

* cited by examiner

Primary Examiner—Glenn K. Dawson
Assistant Examiner—Michael Mendoza
(74) Attorney, Agent, or Firm—McGlew and Tuttle, P.C.

(57) ABSTRACT

A device with a gas sensor for measuring a breathing gas component in a breathing gas line is improved such that a pressure correction of the gas concentration measurement can be performed without appreciably affecting the respiration pressure. Provisions are made for branching off a first measuring gas line (23) with a first electrochemical measuring cell (28) from the breathing gas line (7). A first throttling point (26) is arranged in the course of the first measuring gas line (23) between the first electrochemical measuring cell (28) and the breathing gas line (7). A first pressure sensor (29), for the pressure correction, is located downstream of the first electrochemical measuring cell (28).

18 Claims, 1 Drawing Sheet

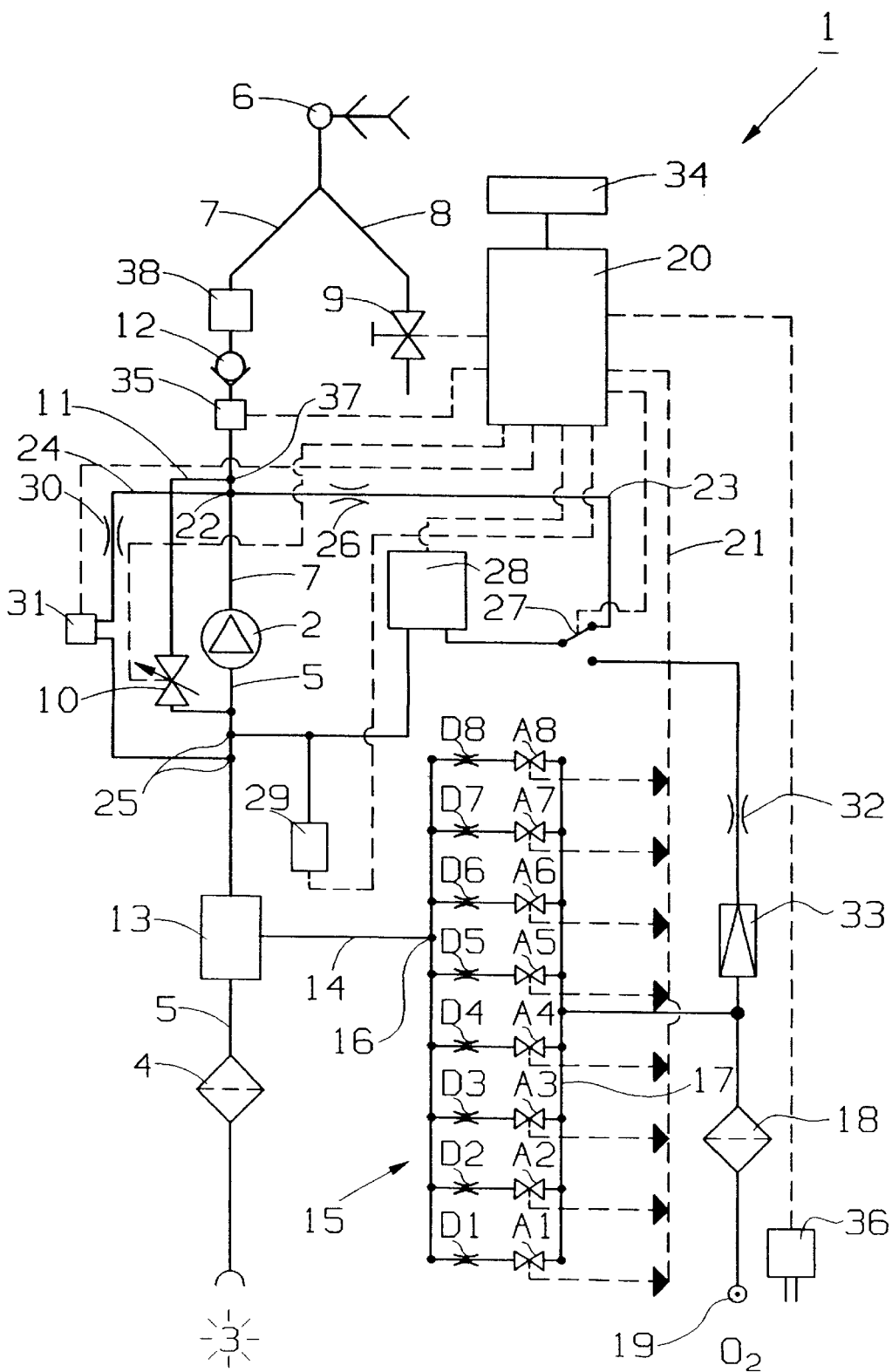

DEVICE FOR MEASURING A BREATHING GAS COMPONENT IN A BREATHING GAS LINE

FIELD OF THE INVENTION

The present invention pertains to a device with a gas sensor for measuring a breathing gas component in a breathing gas line, which is connected via a breathing gas delivery device to a gas supply line for breathing gas and with a bypass line extending from the breathing gas line to the gas supply line.

BACKGROUND OF THE INVENTION

A respirator with a delivery device for breathing gas, which draws in ambient air and pumps it into a breathing gas line leading to a patient, has become known from DE 197 08 094 A1. By returning part of the breathing gas drawn in into the area of the intake side of the delivery device and simultaneously introducing oxygen from an oxygen source into the gas supply line, the oxygen concentration in the breathing gas can be adapted to the patient's needs. The oxygen concentration in the breathing gas is measured with an oxygen sensor in the breathing gas line. In addition to the oxygen concentration, the breathing gas flow and the respiration pressure are determined as well.

Pressure variations occur in the breathing gas line due to the interplay of inspiration and expiration, and they affect the accuracy of the oxygen concentration measurement. Even though it would be possible to calculate correction values for the oxygen concentration by the pressure measurement, which is performed in the vicinity of the oxygen sensor, complicated evaluating logarithms are needed for this, because both the course of the pressure over time and the course of the oxygen concentration over time must be evaluated simultaneously. Correspondingly corrected measured values for the oxygen concentration are therefore available only after a certain time and therefore they also contain a high inaccuracy. If the oxygen sensor is used in the control circuit as an actual value transducer for the oxygen concentration to be set, delays and inaccuracies in the determination of the actual value are not acceptable, because these would compromise the control.

SUMMARY AND OBJECTS OF THE INVENTION

The primary object of the present invention is to improve a respirator of the type described such that a pressure correction of the oxygen concentration measurement can be performed without appreciably affecting of the respiration pressure.

According to the invention, a device is provided with a gas sensor for measuring a breathing gas component in a breathing gas line. The breathing gas line is connected via a breathing gas delivery device to a gas supply line for breathing gas and with a bypass line extending from the breathing gas line to the gas supply line. A first measuring gas line with a first electrochemical measuring cell as a gas sensor is provided in parallel to the bypass line. A first throttling point is provided in the course of the first measuring gas line between the first electrochemical measuring cell and the breathing gas line. A first pressure sensor is located downstream of the first electrochemical measuring cell. A junction point for the first measuring gas line is arranged within the gas supply line upstream of the bypass line.

The advantage of the present invention is essentially that by arranging the oxygen sensor in a measuring gas line leading from the breathing gas line to the gas supply line in the intake area of the breathing gas delivery device and by arranging a throttling point upstream of the first electrochemical measuring cell, a measurement of the oxygen concentration is carried out in the so-called bypass flow without pressure variations in the breathing gas line appreciably affecting the gas flow in the area of the first electrochemical measuring cell. A measuring gas flow, which flows off via the first electrochemical measuring cell into the gas supply line, is branched off from the breathing gas line through the first throttling point. In terms of pressure, the gas supply line is somewhat below the ambient pressure level. The pressure downstream of the first throttling point is determined with a first pressure sensor, which records only slight pressure variations compared with the pressure measurement in the breathing gas line, to which the respiratory pressure is admitted.

The measuring gas flow over the first electrochemical measuring cell is on the order of magnitude of about 200 mL per minute. By returning the measuring gas into the gas supply line, no breathing gas is lost from the breathing gas line.

A second measuring gas line, with a second electrochemical measuring cell, may advantageously be arranged in parallel to the first measuring gas line. The second electrochemical measuring cell is used to monitor the first electrochemical measuring cell, on the one hand, and, on the other hand, it is used as an actual value transducer for the oxygen concentration in case the first electrochemical measuring cell is not active or is in the calibration mode. A second throttling point, with which the second electrochemical measuring cell is uncoupled from the pressure prevailing in the breathing gas line, is arranged between the breathing gas line and the second electrochemical measuring cell within the second measuring gas line.

The branch-off point for the measuring gas line may advantageously be arranged within the breathing gas line before the branch-off point of the bypass line in the direction of flow. It is thus achieved that a pressure, which is higher than the ambient pressure level and ensures the measuring gas flow through the measuring gas lines, is always present at the branch-off point.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The FIGURE is a schematic diagram showing an exemplary embodiment of the present invention.

DESCRIPTION OF THE PREFERRED EMBODIMENT

Referring to the drawings in particular, the only FIGURE shows a respirator 1, in which air is drawn by means of a blower 2 from the environment 3 via a bacteria filter 4 and a gas supply line 5 and is pumped into a breathing gas line leading to a patient 6. The expiration takes place via an expiration line 8 and an expiration valve 9. The expiration valve 9 is closed during the inspiration phase, so that the inspiration pressure can build up in the breathing gas line 7, and it is open during the expiration phase to the extent that the expiration pressure drops to a predetermined end-expiratory residual pressure. The value of the inspiration pressure is set with the blower 2 and with a bypass valve 10 with a bypass line 11, which the bypass valve 10 bridges over the blower 2. The bypass valve 10 is extensively closed during the inspiration phase, so that the breathing gas drawn in is delivered nearly completely to the patient 6 via the breathing gas line 7. The bypass valve 10 is opened at the beginning of the expiration phase, so that the breathing gas is returned to the intake side of the blower 2 via the bypass line 11 and the patient 6 can breath out via the opened expiration valve 9. The breathing gas circulates between the blower 2 and the bypass line 11 during the expiration phase. A nonreturn valve 12 prevents breathing gas from flowing back into the breathing gas line 7 during the expiration. A buffer volume 13, which is connected to a gas-metering unit 15 for oxygen via a feed line 14, is located in the gas supply line 5 between the bacteria filter 4 and the blower 2. The gas-metering unit 15 comprises a parallel circuit of throttling elements D 1, D 2, D 3, D 4, D 5, D 6, D 7, D 8 with shut-off valves A 1, A 2, A 3, A 4, A 5, A 6, A 7, A 8 belonging to them, which are connected to the feed line 14 at a collection point 16, on the one hand, and are supplied with oxygen via a distributor 17, on the other hand. The distributor 17 is connected to a pressurized oxygen gas source 19 via a filter 18. Concerning their throughput capacity, the throttling elements D 1, D 2, D 3, D 4, D 5, D 6, D 7, D 8 are provided with a binary weighting, so that the required oxygen gas flow can be set by appropriately opening and closing individual shut-off valves. The shut-off valves A 1, A 2, A 3, A 4, A 5, A 6, A 7, A 8 receive control pulses for this purpose from a control and regulating unit 20 via a control line 21. The oxygen gas flow can be corrected, if necessary, by cycling individual shut-off valves by generating control pulses with variable cycle frequency and different pulse-to-pause ratios by the control and regulating unit 20. The control and regulating unit 20, which performs all measurement, evaluation and regulation tasks, is likewise connected to the expiration valve 9 and the bypass valve 10.

A branch-off point 22 for a first measuring gas line 23 and a second measuring gas line 24 is arranged in the breathing gas line downstream of the blower 2 and on the incoming flow side of a discharge opening 37. The measuring gas lines 23, 24 extend from the branch-off point 22 to a junction point 25 upstream of the bypass line 11. The junction point 25 is thus essentially at the pressure level prevailing within the buffer volume 13, which deviates only slightly from the pressure prevailing in the environment 3.

Beginning from the branch-off point 22, a first throttling point 26, a changeover switch 27, a first electrochemical measuring cell 28, and a first pressure sensor 29 are arranged in the first measuring gas line 23. The second measuring gas line 24 contains a second throttling point 30 and a second electrochemical measuring cell 31.

A gas connection is established by means of the changeover switch 27 either between the first electrochemical measuring cell 28 and the first throttling point 26 or between the first electrochemical measuring cell 28 and a third throttling point 32, which is connected to a pressurized oxygen gas supply source 19 via a pressure reducer 33. Depending on the position of the changeover switch 27, the first electrochemical measuring cell 28 receives the measuring gas either from the breathing gas line 7 or, for calibration purposes, from the pressurized oxygen gas source 19.

The respirator 1 according to the present invention operates as follows:

Certain respiration parameters, such as the breathing gas flow, the maximum inspiration pressure, the inspiration time, the expiration time, the end-expiratory pressure and the inspiratory oxygen concentration, are entered into the control and regulating unit 20 via an operating unit 34. Preset values for the gas-metering unit 15, the speed of the blower 2, the setting of the bypass valve 10 and the expiration valve 9 are calculated from these. The gas flow is measured by means of a flow meter 35 within the breathing gas line 7 and the shut-off valves of the gas-metering unit 15 are actuated corresponding to the measured value and the inspiratory oxygen concentration set such that a corresponding oxygen concentration will become established in the breathing gas. The oxygen concentration downstream of the blower 2 is determined with the first electrochemical measuring cell 28. Due to the dynamic pressure building up before the discharge opening 37 of the bypass line 11 during the inspiration, a first measuring gas flow is sent through the first measuring gas line 23 to the first electrochemical measuring cell 28 via the first throttling point 26. The pressure downstream of the first electrochemical measuring cell 28 is determined with the first pressure sensor 29 for the pressure correction of the measured oxygen concentration, which correction is to be performed. The first pressure sensor 29 is located in the FIGURE between the junction point 25 and the first electrochemical measuring cell 28.

Variations in the outer ambient pressure are measured by a second pressure sensor 36 located outside the lines 5, 7 and are integrated by the control and regulating unit 20 in the pressure correction of the measured value delivered by the first electrochemical measuring cell 28.

A second measuring gas flow flows from the branch-off point 22 through the second measuring gas line 24 and via the second throttling point 30 and the second electrochemical measuring cell 31 to the junction point 25 within the gas supply line 5. The pressure correction of the concentration measured value determined by the second electrochemical measuring cell 31 is performed with the first pressure sensor 29 with the inclusion of the second pressure sensor 36.

The second electrochemical measuring cell 31 is used essentially to monitor the first electrochemical measuring cell 28. The measured oxygen concentration values determined by the electrochemical measuring cells 28, 31 are read into the control and regulating unit 20 for this purpose and checked for plausibility there. The oxygen concentration within the breathing gas line 7 is monitored by means of a control circuit, not shown in detail in the FIGURE, in which the actual value of the oxygen concentration is measured with the first electrochemical measuring cell 28, a manipulated variable is generated with the inclusion of the preset value for the oxygen concentration, which preset value is entered into the control unit 20 via the operating unit 34, and it is transmitted to the gas-metering unit 15 via the control line 21. The measured value determined by the flow meter 35 is included in the manipulated variable such that, corresponding to a flow-proportional metering of oxygen into the buffer volume 30, the oxygen gas flow is proportionally increased at higher gas flows and is correspondingly reduced at lower gas flows. The oxygen concentration can be set at first approximately at the preset value by the flow-proportional metering of oxygen, the fine adjustment being performed based on the oxygen concentration measurement by means of the first electrochemical measuring cell 28.

In case of failure of the first electrochemical measuring cell 28, the second electrochemical measuring cell 31 is used as the actual value transducer. The second electrochemical measuring cell 31 is also used to control the oxygen concentration when the first electrochemical measuring cell 28 is in the calibration mode. For calibration, the first electrochemical measuring cell 28 is connected to the pressurized oxygen gas source 19 by means of the changeover switch 27 via the third throttling point 32. Due to the presence of two electrochemical measuring cells, the operation of the respirator 1 is guaranteed even when one of the electrochemical measuring cells must be briefly switched off for calibration purposes or when the one electrochemical measuring cell is to be replaced.

A dynamic pressure is built up upstream of the discharge opening 37 of the bypass line 11 at the throttling points 26, 30 during the inspiration phase and also during the expiration due to the arrangement of the branch-off point 22 upstream of the discharge opening 37 of the bypass line 11, and even though this dynamic pressure varies, it leads to a permanent measuring gas flow through the measuring gas lines 23, 24. The cross-sectional areas of the throttling points 26, 30 are dimensioned such that a mean measuring gas flow of about 200 mL per minute becomes established. The measuring gas flows approximately under ambient pressure conditions via the junction point 25 into the gas supply line 5 and the buffer volume 13 and is again drawn in there together with the ambient air and the oxygen introduced by the gas-metering unit 15 into the buffer volume 13 and is fed to the patient 6. Thus, no measuring gas is lost. Effective uncoupling of the electrochemical measuring cells 28, 31, from the pressure prevailing in the breathing gas line 7, is achieved by means of the throttling points 26, 30.

A breathing gas humidifier 38, which is designed as an electrically heated humidifier and with which the breathing air is adapted to the natural conditions of the patient 6, is located in the breathing gas line 7 downstream of the nonreturn valve 12.

While a specific embodiment of the invention has been shown and described in detail to illustrate the application of the principles of the invention, it will be understood that the invention may be embodied otherwise without departing from such principles.

What is claimed is:

1. A breathing device, comprising:
   a breathing gas delivery device;
   a gas supply line for breathing gas;
   a breathing gas line connected via said breathing gas delivery device to said gas supply line;
   a gas sensor for measuring a breathing gas component in said breathing gas line,
   a bypass line extending from said breathing gas line to said gas supply line;
   a measuring gas line with an eletrochemical measuring cell gas sensor generating a gas value signal, said measuring gas line being provided in parallel to said bypass line;
   a throttling point provided in the course of said measuring gas line between said electrochemical measuring cell gas sensor and said breathing gas line;
   a pressure sensor located downstream of said electrochemical measuring cell gas sensor, said pressure sensor generating a pressure value signal;
   a measuring gas line and gas supply line junction point provided upstream of said bypass line;
   a control unit forming a correction value for said gas value signal with said pressure value signal.

2. A device in accordance with claim 1, further comprising:
   another measuring gas line with another electrochemical measuring cell gas sensor arranged between said breathing gas line and said measuring gas line and gas supply line junction point; and
   another throttling point provided in the course of said another measuring gas line, located upstream of said another electrochemical measuring cell gas sensor.

3. A device in accordance with claim 1, further comprising:
   another pressure sensor measuring the atmospheric pressure; and
   a control unit, said control unit receiving a measured value signal from said another pressure sensor and forming a correction value for the pressure sensor with the measured value signal of said another pressure sensor.

4. A device in accordance with claim 2, further comprising:
   another pressure sensor measuring the atmospheric pressure; and
   a control unit, said control unit receiving a measured value signal from said another pressure sensor and forming a correction value for the pressure sensor with the measured value signal of said another pressure sensor.

5. A device in accordance with claim 1, further comprising:
   a branch-off point for said measuring gas line arranged along said breathing gas line upstream of a discharge opening of said bypass line.

6. A device in accordance with claim 2, further comprising:
   a branch-off point for said measuring gas line and for said another measuring gas line said branch-off point being arranged along said breathing gas line upstream of a discharge opening of said bypass line.

7. A device in accordance with claim 1, further comprising:
   a calibration source; and
   a changeover switch arranged within said measuring gas line such that said electrochemical measuring cell gas sensor can be connected to said calibration source.

8. A device in accordance with claim 2, further comprising:
   a calibration source; and
   a changeover switch arranged within said measuring gas line such that said electrochemical measuring cell gas sensor can be connected to said calibration source.

9. A breathing device in accordance with claim 1, wherein;
   said gas delivery device receives the breathing gas from said gas supply line, pressurizes the breathing gas, and delivers pressurized breathing gas to said breathing gas line.

10. A breathing device comprising:
    a supply line for supplying breathing gas;
    a breathing gas delivery device connected to said supply line, receiving the breathing gas from the supply line, and pressurizing the breathing gas;
    a breathing gas line connected to said delivery device and receiving pressurized breathing gas from said delivery device;
    a measuring line connected to said supply line at a supply junction point and to said breathing gas line at a branch off point;

a gas sensor arranged in said measuring line, said gas sensor generating a gas value signal, a throttling point arranged in said measuring line between said breathing gas line and said gas sensor, a pressure sensor arranged in said measuring line between said supply line and said gas sensor, said pressure sensor generating a pressure value signal;

a control unit forming a correction value for said gas value signal with said pressure value signal.

11. A breathing device in accordance with claim 10, further comprising:

a bypass line having a connection to said supply line arranged downstream of said supply junction point, said bypass line also being connected to said breathing gas line.

12. A breathing device in accordance with claim 11, wherein:

said bypass line has a connection to said breathing gas line arranged downstream of said branch off point.

13. A breathing device in accordance with claim 10, wherein:

said gas sensor senses a type of gas.

14. A breathing device in accordance with claim 10, wherein said gas sensor is an electrochemical measuring cell gas sensor;

said breathing gas line is connectable to a patient.

15. A device in accordance with claim 10, further comprising:

another measuring gas line connected to said supply line at said supply junction point and to said breathing gas line at said branch off point;

another gas sensor arranged in said another measuring line;

another throttling point arranged in said another measuring line between said breathing gas line and said another gas sensor.

16. A device in accordance with claim 10, further comprising:

another pressure sensor measuring atmospheric pressure; and a control unit, said control unit receiving a measured value signal from said another pressure sensor and forming another correction value for said pressure sensor with said measured value signal of said another pressure sensor.

17. A device in accordance with claim 15, further comprising:

another pressure sensor measuring the atmospheric pressure; and a control unit, said control unit receiving a measured value signal from said another pressure sensor and forming another correction value for the pressure sensor with the measured value signal of said another pressure sensor.

18. A device in accordance with claim 10, further comprising:

a calibration source; and a changeover switch arranged within said measuring gas line such that said gas sensor can be connected to said calibration source.

* * * * *